(12) United States Patent
Cascio

(10) Patent No.: US 7,806,878 B2
(45) Date of Patent: Oct. 5, 2010

(54) MEDICAMENT APPLICATOR

(76) Inventor: Gregory R. Cascio, 3437 N. Hoyne, Chicago, IL (US) 60618

( * ) Notice: Subject to any disclaimer, the term of this patent is extended or adjusted under 35 U.S.C. 154(b) by 123 days.

(21) Appl. No.: 11/873,884

(22) Filed: Oct. 17, 2007

(65) Prior Publication Data

US 2009/0105672 A1   Apr. 23, 2009

(51) Int. Cl.
*A61M 35/00* (2006.01)
(52) U.S. Cl. ...................................... 604/310
(58) Field of Classification Search ............. 604/289, 604/290, 310; 132/109, 218, 277
See application file for complete search history.

(56) References Cited

U.S. PATENT DOCUMENTS

| | | | |
|---|---|---|---|
| 1,382,586 A * | 6/1921 | Wilson | 132/110 |
| 3,291,129 A | 12/1966 | Burelle et al. | |
| 4,183,328 A | 1/1980 | Lawrence | |
| 4,608,045 A | 8/1986 | Fretwell | |
| 4,678,463 A | 7/1987 | Millar | |
| 5,098,291 A | 3/1992 | Curtis et al. | |
| 5,320,600 A | 6/1994 | Lambert | |
| 5,339,839 A | 8/1994 | Forcelledo et al. | |
| 6,035,806 A | 3/2000 | Lorenzo | |
| 6,035,863 A * | 3/2000 | Mao | 132/273 |
| 6,539,949 B2 | 4/2003 | Christensen | |
| 7,059,333 B2 | 6/2006 | Duqueroie | |
| 2003/0226519 A1 | 12/2003 | Burridge et al. | |
| 2004/0071494 A1 | 4/2004 | Staniforth et al. | |
| 2006/0011666 A1 * | 1/2006 | Wurtz et al. | 222/541.1 |
| 2006/0200069 A1 | 9/2006 | Cormier et al. | |
| 2007/0149945 A1 | 6/2007 | Wilkinson et al. | |

OTHER PUBLICATIONS

U.S. Appl. No. 12/203,874, filed Sep. 3, 2008 (which is not being furnished herewith, pursuant to the Commissioner's Notice dated Sep. 21, 2004).
International Search Report and Written Opinion dated Feb. 23, 2009 for International Application No. PCT/US2008/080208.

* cited by examiner

*Primary Examiner*—Tatyana Zalukaeva
*Assistant Examiner*—Benedict L Hanrahan
(74) *Attorney, Agent, or Firm*—James P. Muraff; Neal, Gerber & Eisenberg LLP

(57) ABSTRACT

A medicament applicator for use with a medicament cartridge is disclosed herein. The applicator comprises a first handle member and a second handle member, both of which are movable with respect to one another between a first handle position and a second handle position. The applicator further comprises a first separating member and a second separating member, which are movable between a first separating position, which corresponds to the first handle position, and a second separating position, which corresponds to the second handle position. The applicator further comprises a compressing apparatus attached to the applicator, which compresses the medicament cartridge and selectively expels the medicament from the medicament cartridge.

16 Claims, 14 Drawing Sheets

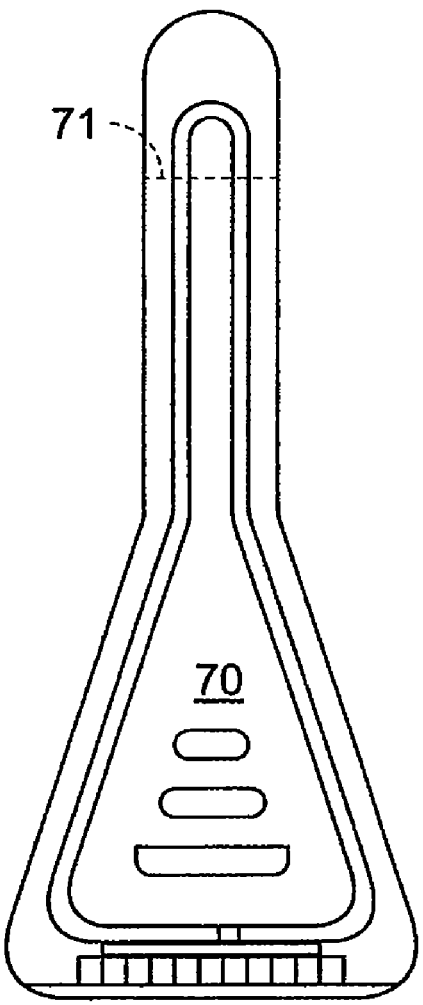
Fig. 3
Fig. 4

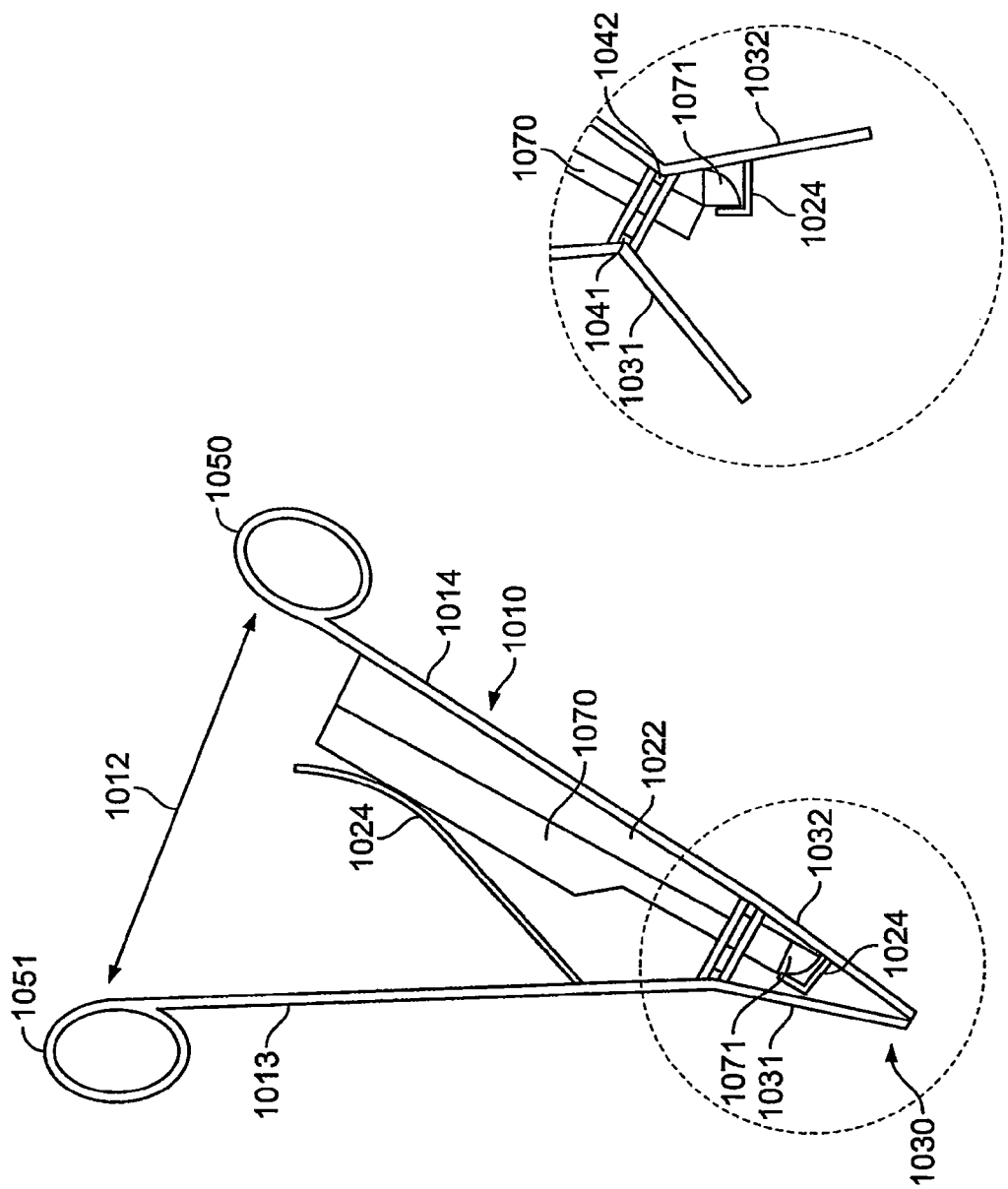

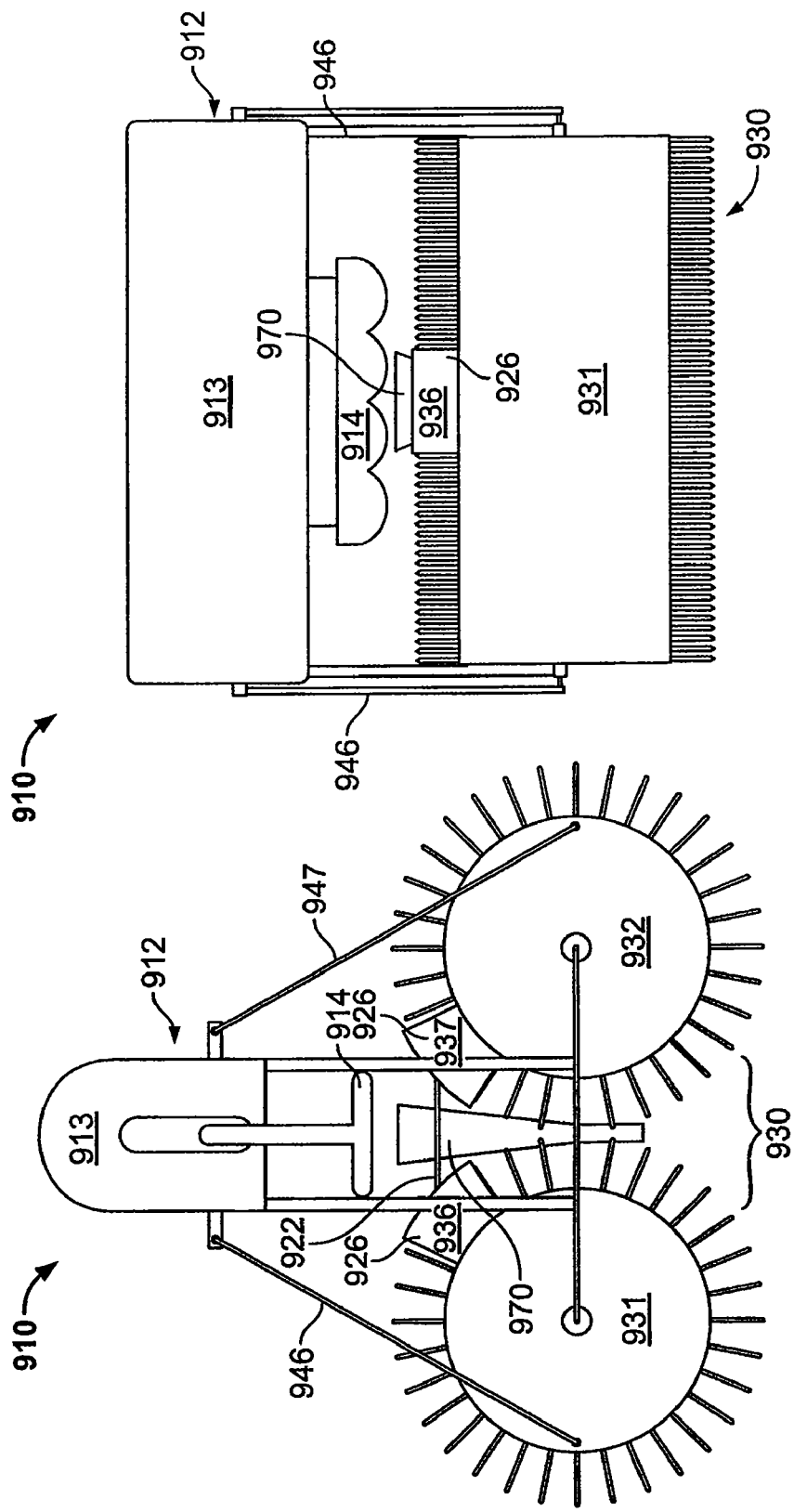

MEDICAMENT APPLICATOR

FIELD OF THE INVENTION

This invention relates to a medicament applicator, such as for use with animals and such as for applying the medicament to skin.

SUMMARY OF THE INVENTION

A medicament applicator is described herein. The details of the invention are set forth below in connection with the detailed description of the embodiments.

BRIEF DESCRIPTION OF THE DRAWINGS

FIG. 3 is a side view of an exemplary medicament cartridge.

FIG. 4 is a front view of the exemplary medicament cartridge set forth in FIG. 3.

FIG. 18 is a side view of the ninth embodiment of the present invention.

FIG. 19 is a close up of the separating apparatus of the embodiment depicted in FIG. 18.

FIG. 21 is a front-end view of an eleventh embodiment of the present invention.

FIG. 22 is a side view of the eleventh embodiment as seen in FIG. 21.

DETAILED DESCRIPTION OF THE DRAWINGS

The present invention is described herein with respect to exemplary medicament applicators that dispense medicament directly to a substrate without requiring the user to touch the medicament. It will be understood that various other applicators can be used in accordance with the present invention. By way of example, and in no way limiting, one use of the present invention would be to expose the skin of an animal by temporarily displacing the fur of the animal, in order to dispense medicament, such as flea or tick medicine, directly to the skin of an animal.

Figure 1:
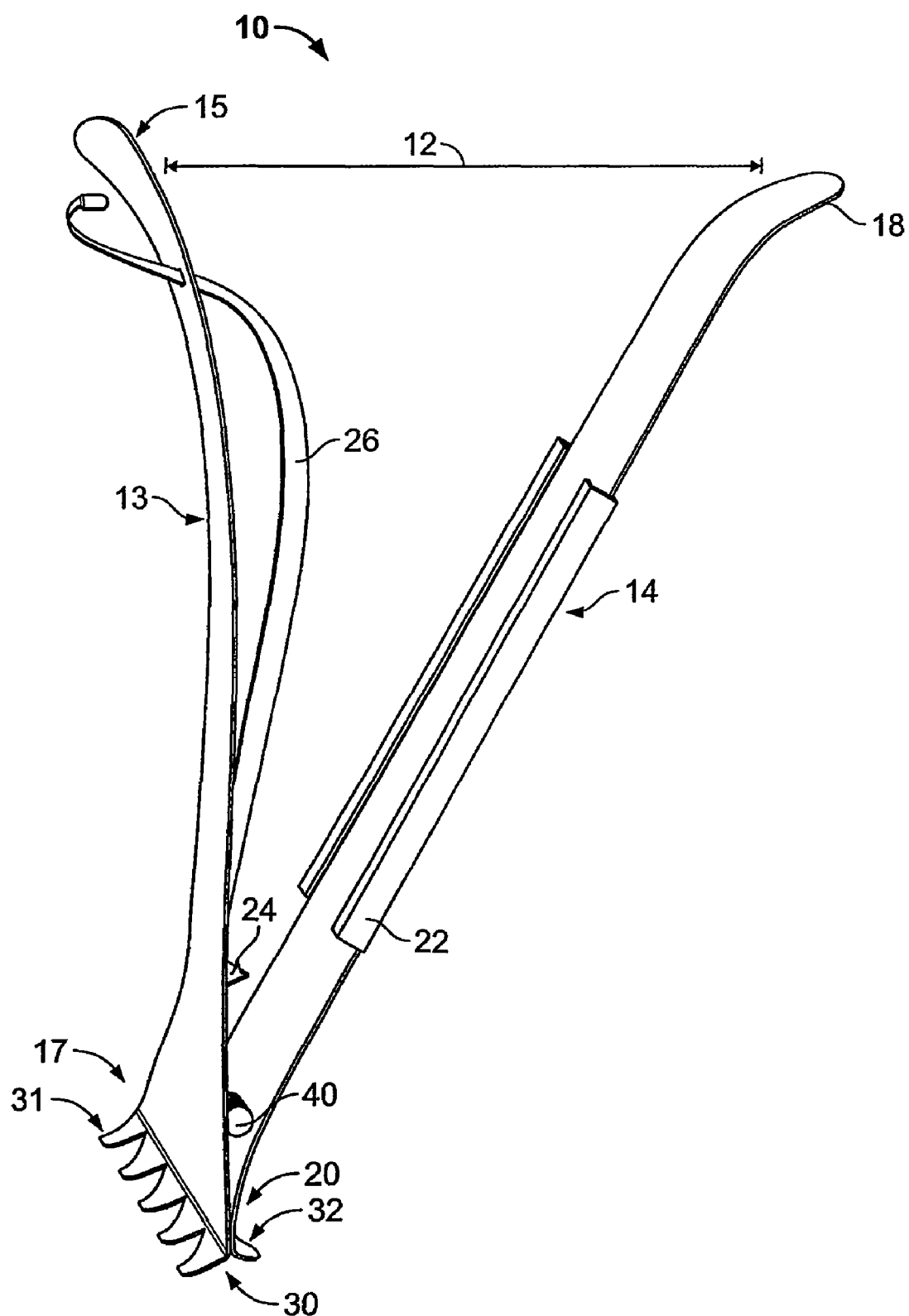
FIG. 1 is a perspective view of a first embodiment of the present invention.

In the embodiment depicted in FIG. 1, applicator 10 comprises handle apparatus 12, which comprises first handle member 13 and second handle member 14. First handle member 13 comprises first end 15, which forms a first gripping portion 16, and second end 17, opposite first end 15. Second handle member 14 comprises first end 18, which forms second gripping portion 19, and second end 20, opposite first end 18.

In order to facilitate the parting of hair, fur, or other material above the substrate, applicator 10 further comprises separating apparatus 30. In the first embodiment, separating apparatus 30 comprises first hair comb 31, which is integrally formed from first handle member 13, and second hair comb 32, which is integrally formed from second handle member 14. Separating apparatus 30 is movable between a first, unopened separating position (shown in Fig. A), and a second, opened separating position. As described more fully below, the first and second separating positions correspond to first and second handle member positions.

As stated above, applicator 10 can be used with a medicament cartridge, such as cartridge 70, shown in FIGS. 3 and 4. In order to better facilitate the use of such a cartridge, applicator 10 further comprises retainer 22, opening apparatus 24 and compressing apparatus 26. Retainer 22 is formed on second handle member 14. In use, a medicament cartridge (not shown) is placed in, and secured by, retainer 22. In the depicted embodiment, retainer 22 is integrally formed from second handle member 14, but it will be apparent to those in the art that the scope of the present invention includes an embodiment in which retainer 22 is removably secured to second handle member 14.

To aid in the opening of a cartridge, such as medicament cartridge 70, opening apparatus 24 is provided and secured to first handle member 13. In use, opening apparatus 24 engages a medicament cartridge (not shown) and thus opens the cartridge. In the depicted embodiment, opening apparatus 24 is integrally formed from first handle member 13. However, it will be apparent to those in the art that the scope of the present invention includes those embodiments in which the opening apparatus is otherwise secured to first handle member 13. Moreover, it will be apparent that the scope of the present invention further includes those embodiments in which the opening apparatus is secured to other elements of apparatus 10, so long as it opens a cartridge when apparatus 10 is used.

As seen in FIG. 1, opening apparatus 24 opens the cartridge by piercing it. As described more fully below, the scope of the present invention includes those embodiments in which opening apparatus 24 opens the cartridge in any number of ways, including cracking the cartridge, pushing a tip of the cartridge, etc.

To aid in dispensing the medicament, compressing apparatus 26 is provided and secured to first handle member 15. In the embodiment depicted in FIG. 1, compressing apparatus 26 is a tensioned spring, either metal or plastic, which engages a medicament cartridge when the handle members are moved to the second position as described more fully below.

Applicator 10 further comprises hinge member 40. Hinges, such as hinge member 40, are well known throughout the art, and will not be described in detail herein. As seen, hinge member 40 connects handle member 13 and handle member 14 such that they are rotatable with respect to one another between a first handle position and a second handle position. In the first handle position, depicted in FIG. 1, first ends 15 and 18 of respective handle members 13 and 14, are apart, while second ends 17 and 20 are together. In the second handle position (not shown), first ends 15 and 18 are together, while second ends 17 and 20 are separated. It will be appreciated that applicator 10 may further comprise a biasing spring (not shown) to bias the handle members to the first handle position.

Figure 9:
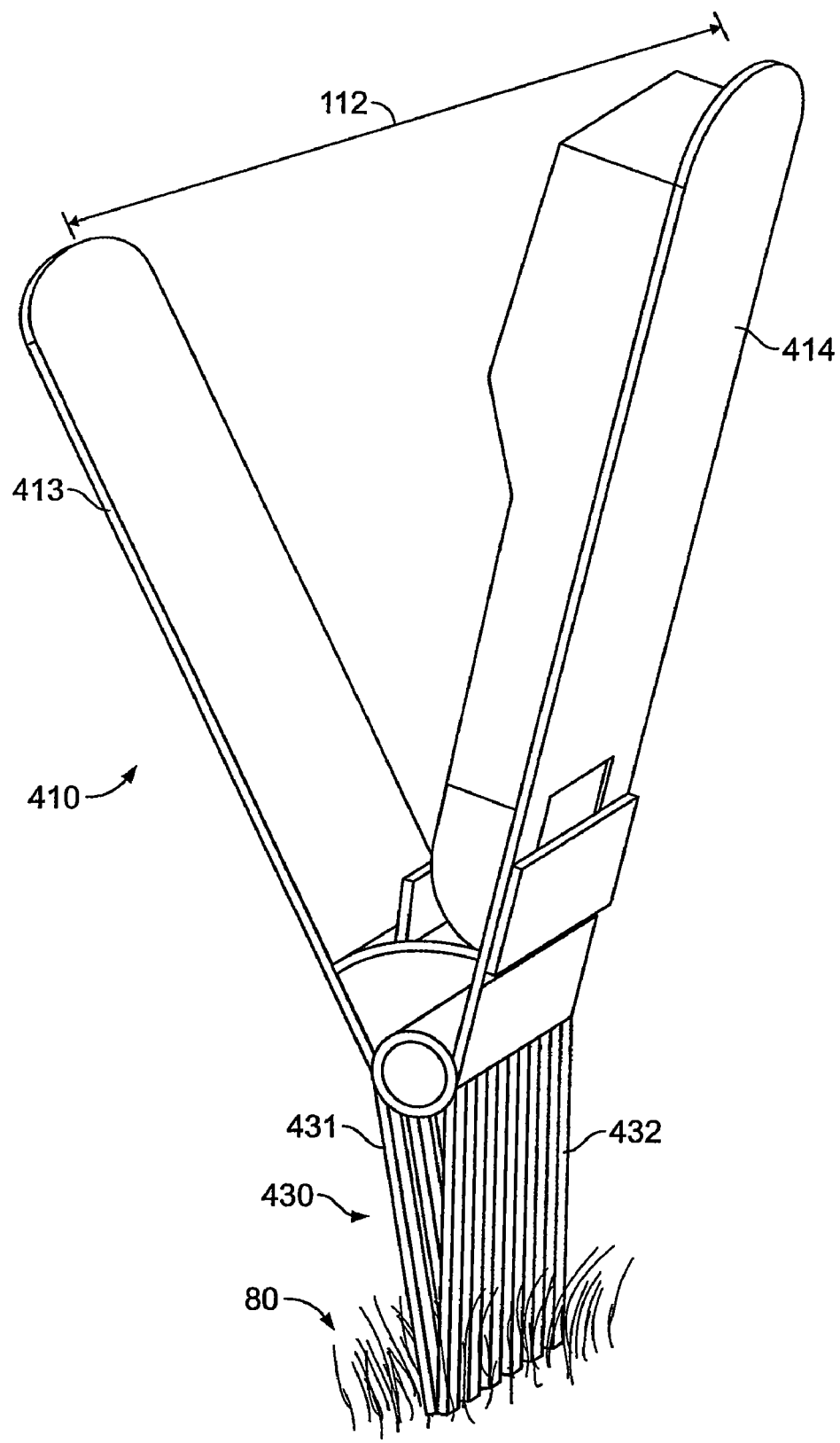
FIG. 9 is a perspective view of a fifth embodiment of the present invention in use and in the first, unopened position.
Figure 10:
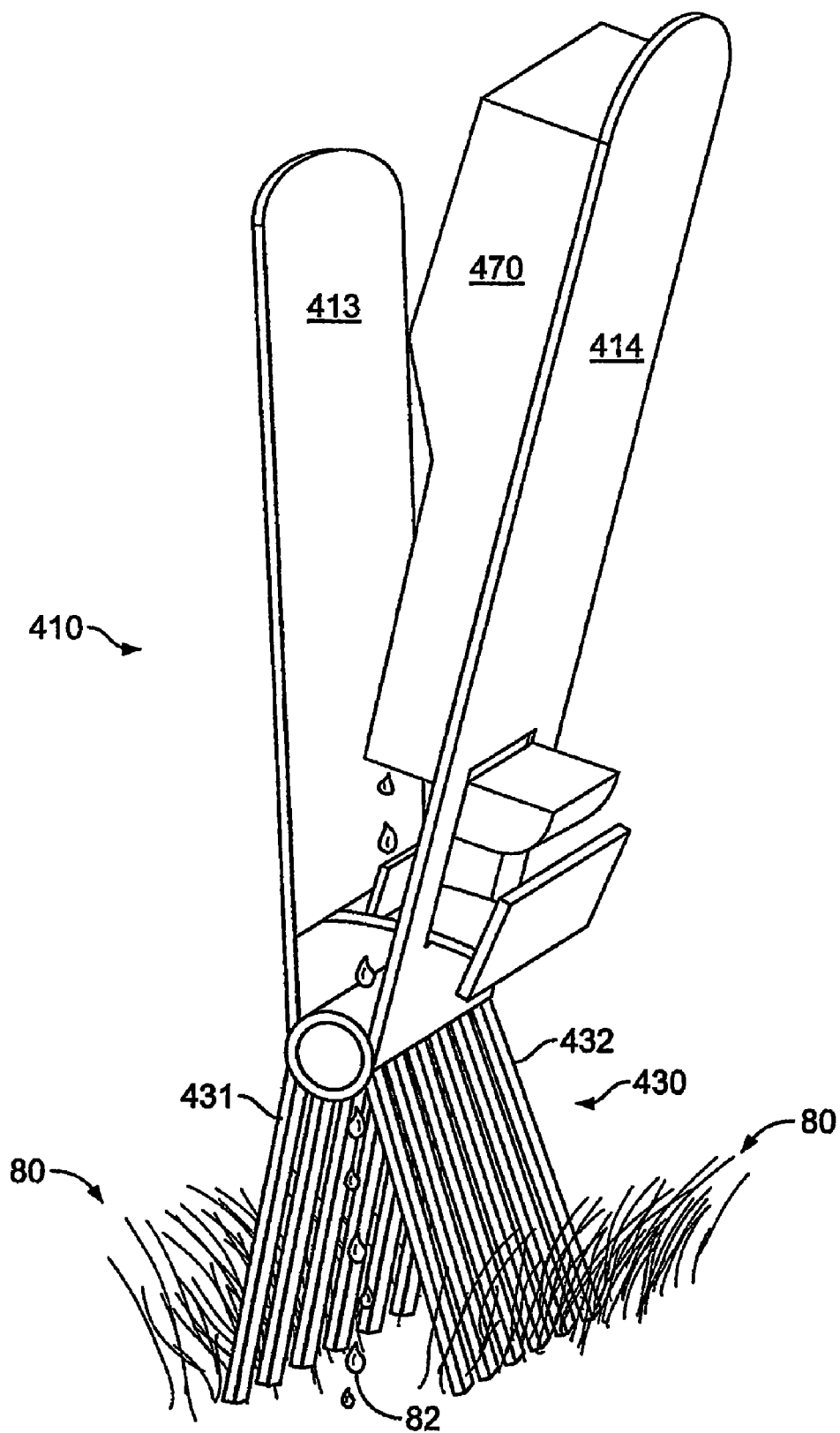
FIG. 10 is a perspective view of the exemplary embodiment as seen in FIG. 9, in use and in the second, opened position.

Applicator 10 is used in a similar way as the embodiment depicted in FIGS. 9 and 10. While the embodiment in FIGS. 9 and 10 differs from the first embodiment, the use of the embodiments is similar, and therefore, FIGS. 9 and 10 can be used as a reference.

In use, applicator 10 works as follows. The user places a medicament cartridge in retainer 22. The user next places both brushes 31 and 32 of separating apparatus 30 on an animal, a person's head, or any other object that comprises a substrate to which the medicament must be applied. The user then compresses handle members 13 and 14, moving them from the first handle position to the second handle position. This causes hair brushes 31 and 32 to separate, parting any hair engaged to or proximate the hair brushes 31 and 32, exposing the skin (or other substrate) underneath. Moving handle members 13 and 14 to the second handle position also causes compressing apparatus 26 to engage the medicament cartridge, and opening member 24 to engage and open the medicament cartridge. In this way, once the skin (or other substrate) has been exposed, the medicament contained in the cartridge can be expelled directly to the skin. It will be appreciated by those in the art that the scope of the present invention includes an embodiment in which a compressing apparatus, such as compressing apparatus 26, first engages a medicament cartridge, then a user selectively compresses the compressing apparatus, thus expelling the medicament.

The remaining embodiments each comprise similar elements as those comprised by applicator 10. As such, each embodiment will only briefly be described herein. Furthermore, the elements that are similar among the embodiments have similar reference numerals. By way of example, element 15 of applicator 10 will be similar to element 115 of applicator 110, element 215 of applicator 210, etc.

Figure 2:
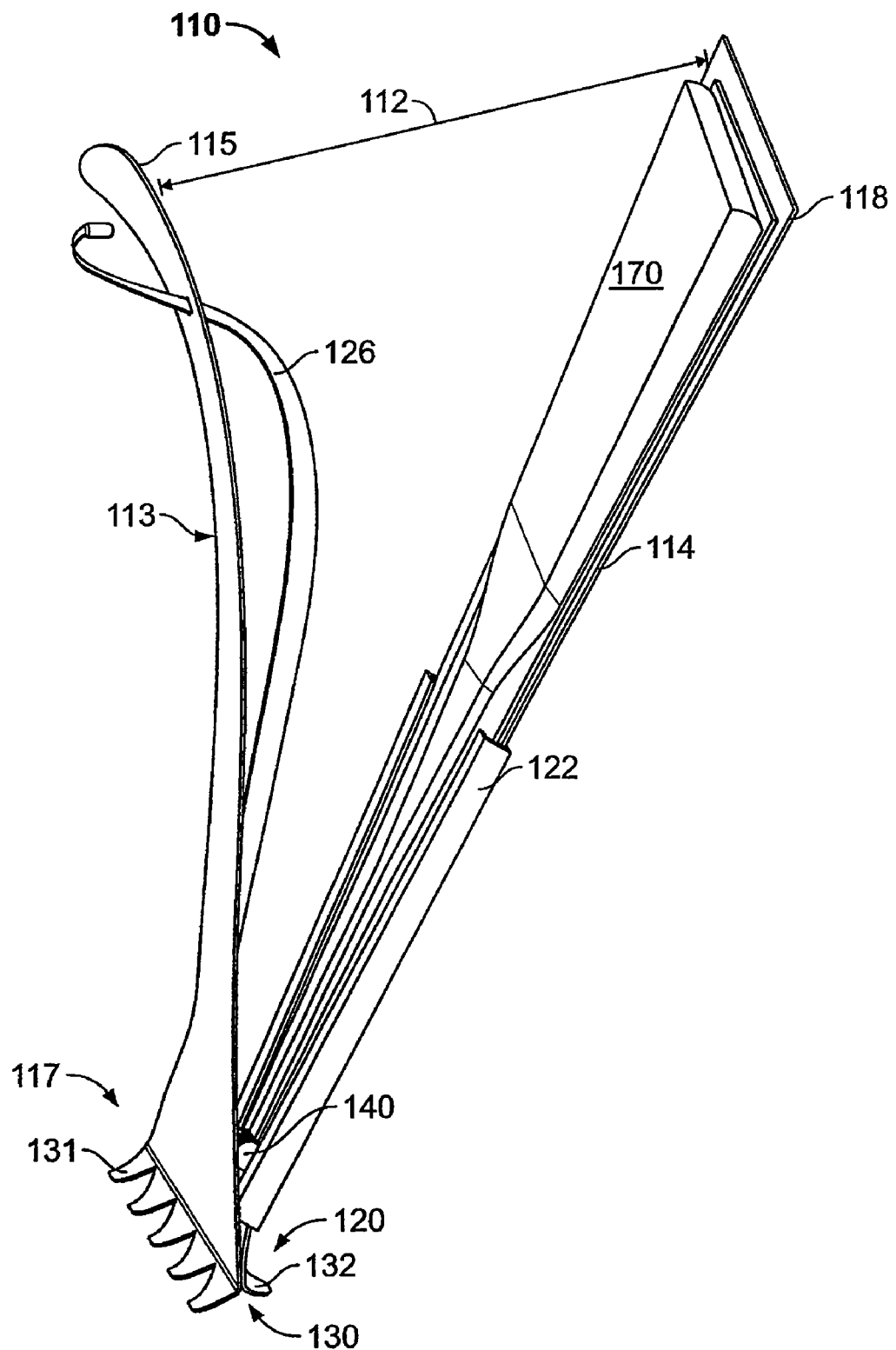
FIG. 2 is a perspective view of a second embodiment of the present invention, including a medicament cartridge.

FIG. 2 depicts a second embodiment of the present invention. As seen, applicator 110 closely resembles applicator 10 depicted in FIG. 1, and comprises many similar elements. By way of example, applicator 110 comprises handle apparatus 112, which comprises first handle member 113 and second handle member 114. Separating apparatus 130 comprises first hair brush 131 and second hair brush 132, both of which are engaged to second ends 117 and 120, respectively, of handle members 113 and 114, respectively. Applicator 110 further comprises compressing apparatus 126 engaged to first handle member 113, and retainer 122 engaged to second handle member 114. Applicator 110 further comprises medicament cartridge 170. As seen, medicament cartridge 170 is engaged to, and retained by, retainer 122. In this manner, applicator 110 may be used repeatedly, and only cartridge 170 must be replaced after each application.

In each of the above embodiments, and in each of the embodiments that are described below, the medicament cartridge is removably secured to the applicator in some manner. Because of this, the same applicator can be repeatedly used, and only a new cartridge need be purchased or employed between uses. It will be appreciated by those in the art, however, that the scope of the present invention includes those embodiments in which a medicament applicator is integrally formed on an applicator. In those embodiments, the entire applicator may be disposed after an application.

FIGS. 3 and 4 depict an exemplary medicament cartridge 70. It will be appreciated by those in the art that the scope of the present invention is not limited to the shape of cartridge 70. Moreover, as described more fully below, cartridge 70 is opened by cracking seal 71. However, it will be appreciated by those in the art that the scope of the present invention includes any method of opening a medicament cartridge such as cartridge 70.

Figure 5:
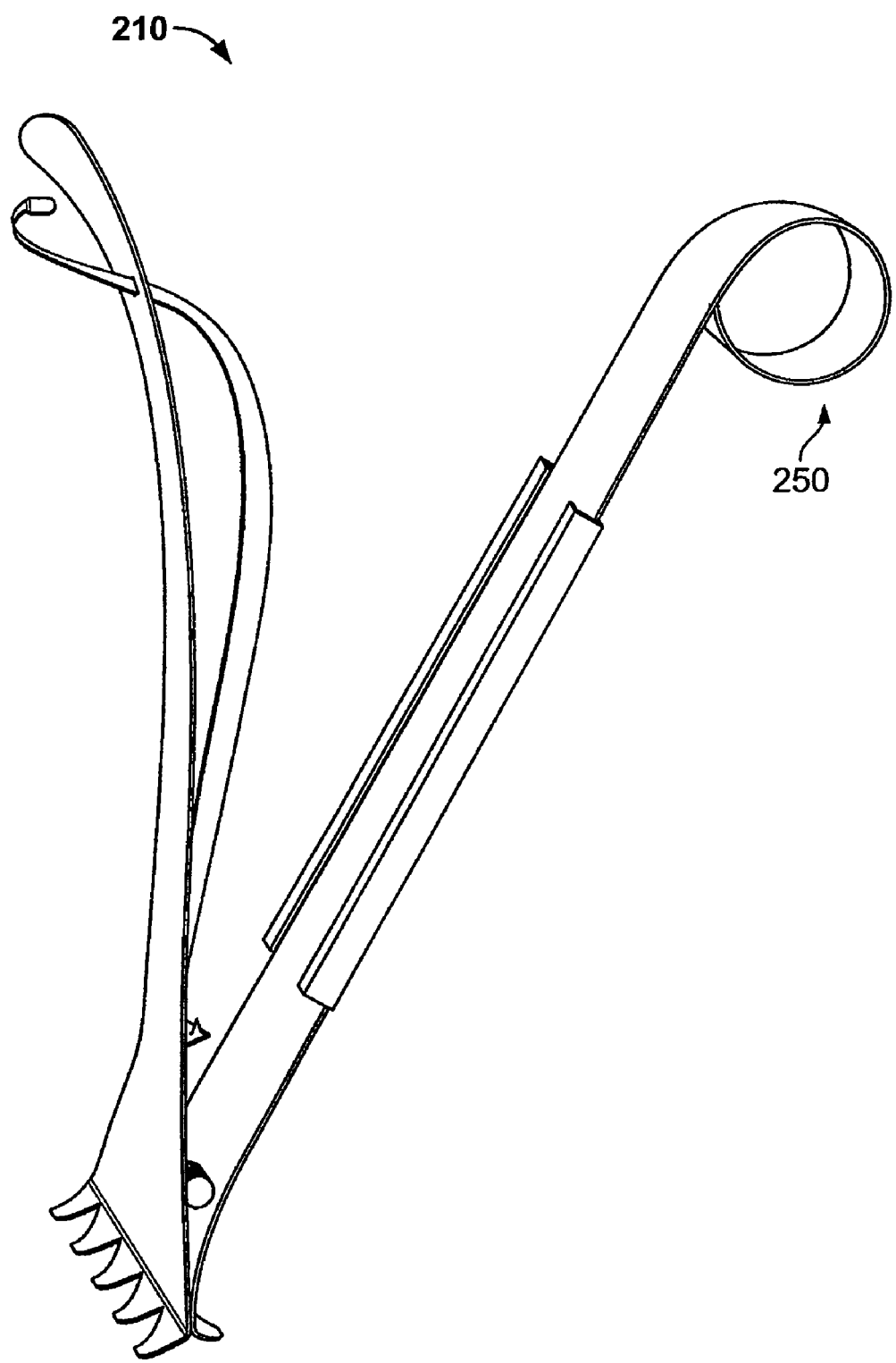
FIG. 5 is a perspective view of a third embodiment of the present invention.

A third embodiment of the present invention is depicted in FIG. 5. Applicator 210 is nearly identical to applicator 10 depicted in FIG. 1. However, in order to provide a grip for the user, a finger loop 250 is formed on second end 218 of second handle member 214.

Figure 6:
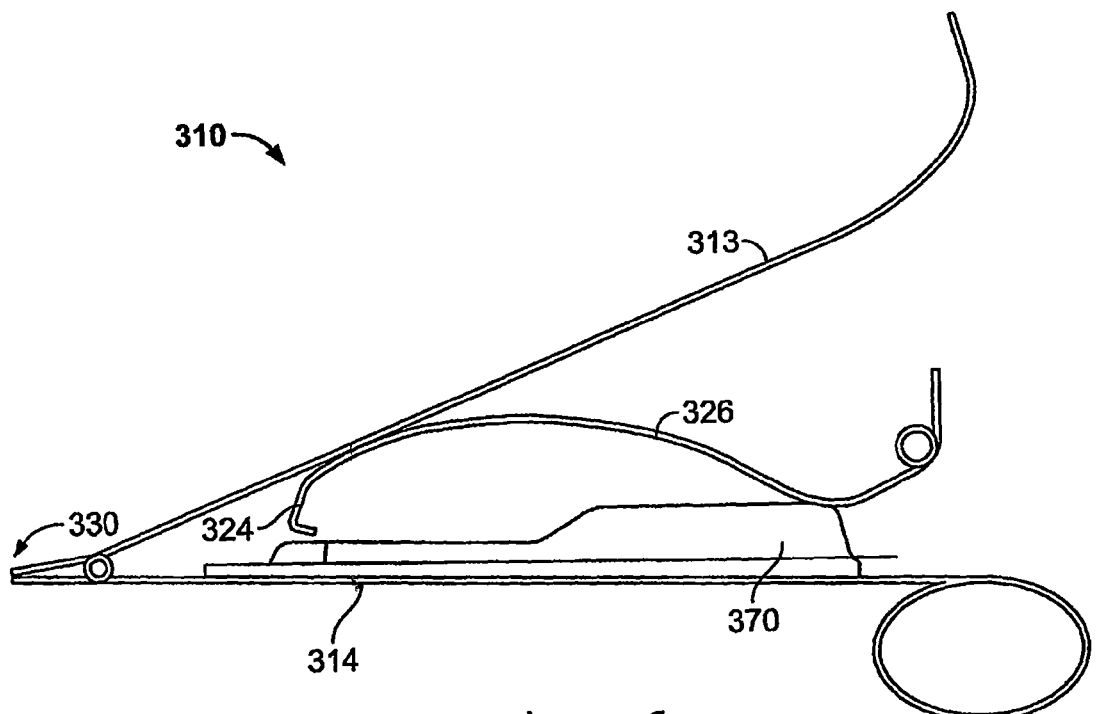
FIG. 6 is a side view of a fourth embodiment of the present invention, including a medicament cartridge.
Figure 7:
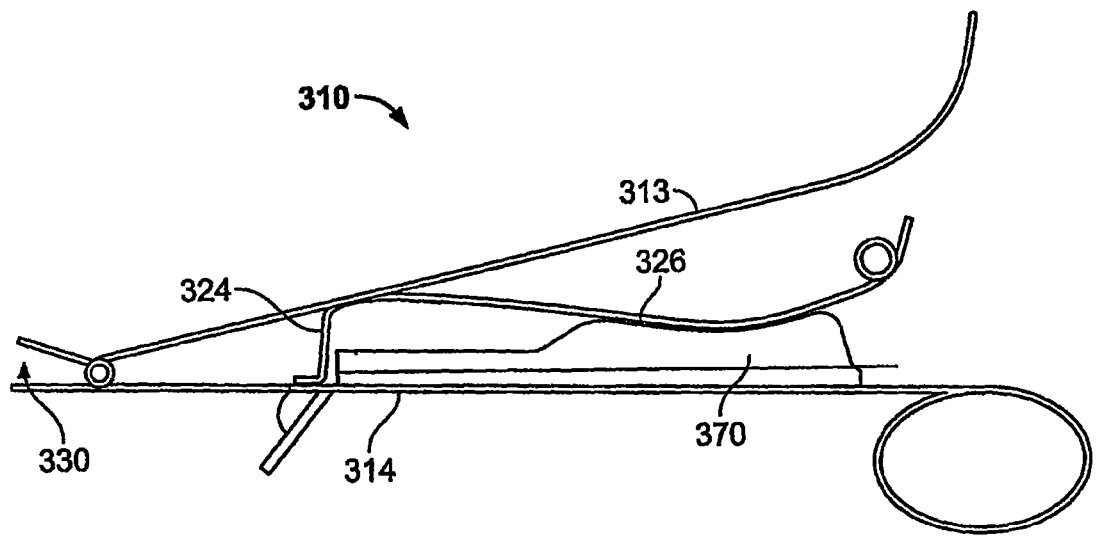
FIG. 7 is a side view of the fourth embodiment of the present invention of FIG. 6, where the medicament cartridge has been opened.

FIGS. 6 and 7 depict a fourth embodiment of the present invention. As seen, applicator 310 comprises similar elements to those disclosed in the previous embodiments. By way of example, and in no way limiting, applicator 310 comprises first handle member 313, second handle member 314, separating apparatus 330, and medicament cartridge 370. In the embodiment depicted in FIGS. 6 and 7, compressing apparatus 326 and opening apparatus 324 are formed as a single element. In the first handle position, depicted in FIG. 6, opening apparatus 324 is not engaged to medicament cartridge 370. While compressing apparatus 326 is shown engaged to cartridge 370, it will be understood by those in the art that compressing apparatus 326 is comprised of flexible metal or plastic and, as such, can be disengaged from cartridge 370 temporarily in order to install or remove cartridge 370 from applicator 310.

When handle members 313 and 314 are moved to the second handle position, as depicted in FIG. 7, opening apparatus 324 engages and opens cartridge 370. As seen, opening apparatus 324 opens cartridge 370 by "cracking" a seal formed on cartridge 370. It will be appreciated by the art that the scope of the present invention includes any means by which opening apparatus 324 can engage and open medicament cartridge 370. Also shown in FIG. 7, compressing apparatus 326 fully engages, and deforms medicament cartridge 370, expelling the medicament from cartridge 370.

Figure 8:
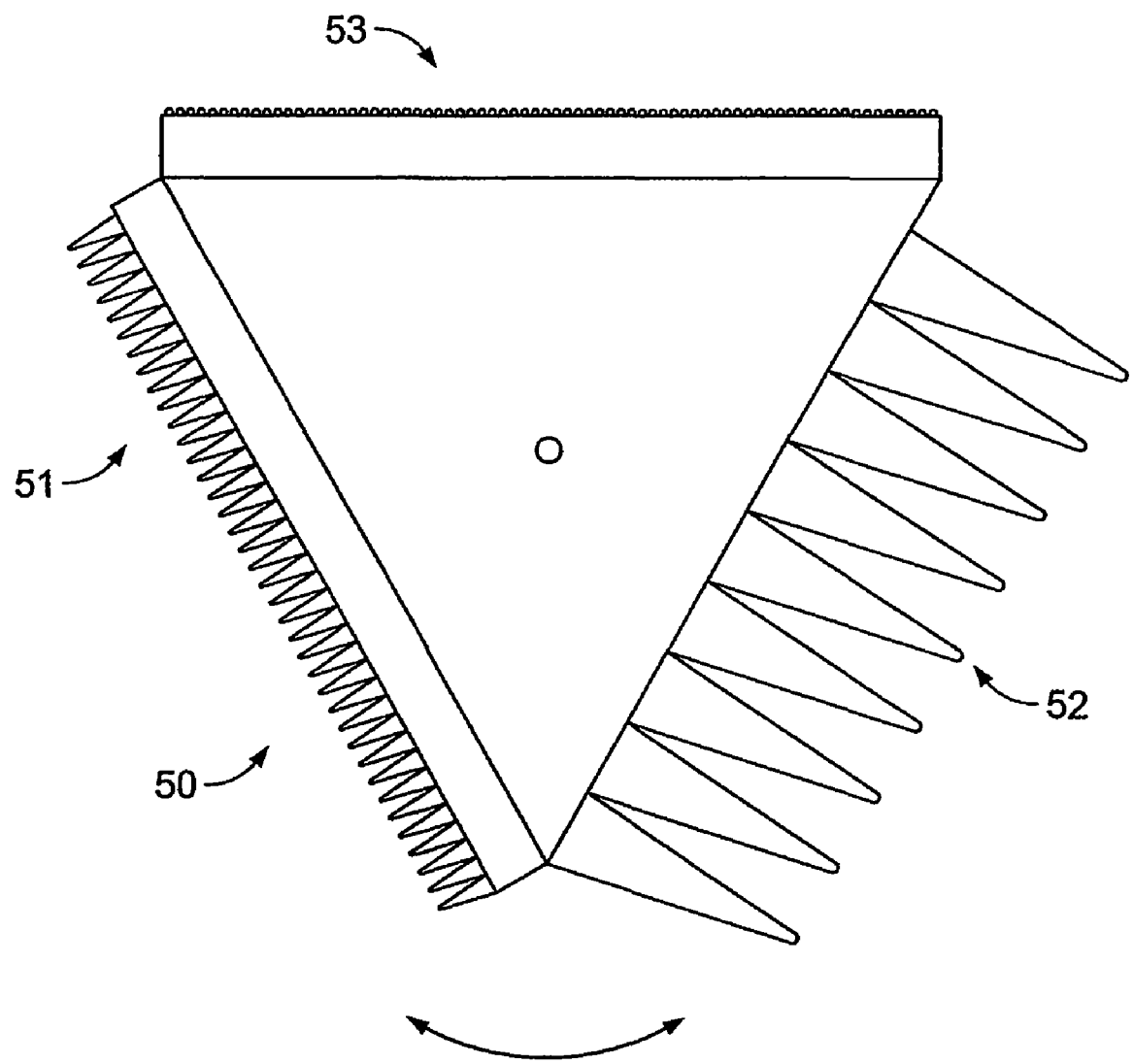
FIG. 8 is a top view of an exemplary changeable head.

It may be desirable to provide an embodiment of the present invention with a means by which the applicator can accommodate different hair lengths using the same basic structure. To that end, FIG. 8 depicts an embodiment of a hair brush similar to hair brushes 31 and 32 depicted in FIG. 1. Hair brush 50 can be used with any embodiment described herein, except the embodiment depicted in FIGS. 21 and 22, which are described below. As seen, hair brush 50 has a first side 51, a second side 52 and a third side 53. Hair brush 50 is rotatably engaged to any of the embodiments, and each side 51, 52 and 53 has a different comb-tooth length. In this manner, a user can use the same applicator for various animals with differing hair lengths. By way of example, and in no way limiting, a user can use an applicator with hair brush 50 on a short-haired dog, such as a Chihuahua, by rotating hair brush 50 so that third side 53 engages the hair of the animal. The user can then use the same applicator on a long-haired dog, such as a German Shepherd, by rotating hair brush 50 so that second side 52 engages the hair of the animal.

In a second embodiment of an accommodating hair brush, a basic applicator, such as the applicator shown in FIG. 1, may be coupled with a removable guard, or a plurality of removable guards. A pair of base hair brushes, similar to hair brushes 31 and 32, would be formed on the applicator. The base hair brushes would be similar in length and use as side 51 of the embodiment depicted in FIG. 8. In other words, the base hair brushes would be ideal for use with very short hair. The removable guard, or each of a plurality of guards, would then slide over the base hair brushes and lock in place. If one removable guard is used, then it would allow the applicator to be used with hair that is longer than would be ideal with the base hair brushes. If a plurality of guards is used, then each guard would allow the applicator to be used with different hair lengths. The lock could be any one of a known manner, and may include a tongue-in-groove mechanism, slot and tab mechanism, etc.

FIGS. 9 and 10 depict a fifth embodiment of the present invention, and show the invention in use. As seen, an exemplary use of the present invention, but by no way a limiting use, is allowing the user to dispense a medicament, such as a flea or tick medicine, directly to the skin of an animal, without touching the medicament. To that end, applicator 410 is shown in use on an animal (not shown) having hair 80. In the first handle position, depicted in FIG. 9, hair brushes 431 and 432 of separating apparatus 430 are closed and placed in hair 80, proximate the skin of the animal (not shown). Once first handle 413 and second handle 414 of handle apparatus 412 are moved to the second handle position, depicted in FIG. 10, medicament cartridge 470 is opened, and simultaneously, hair 80 is parted, exposing the skin of the animal. This allows medicament 82 to be delivered directly to the skin of the animal.

Figure 11:
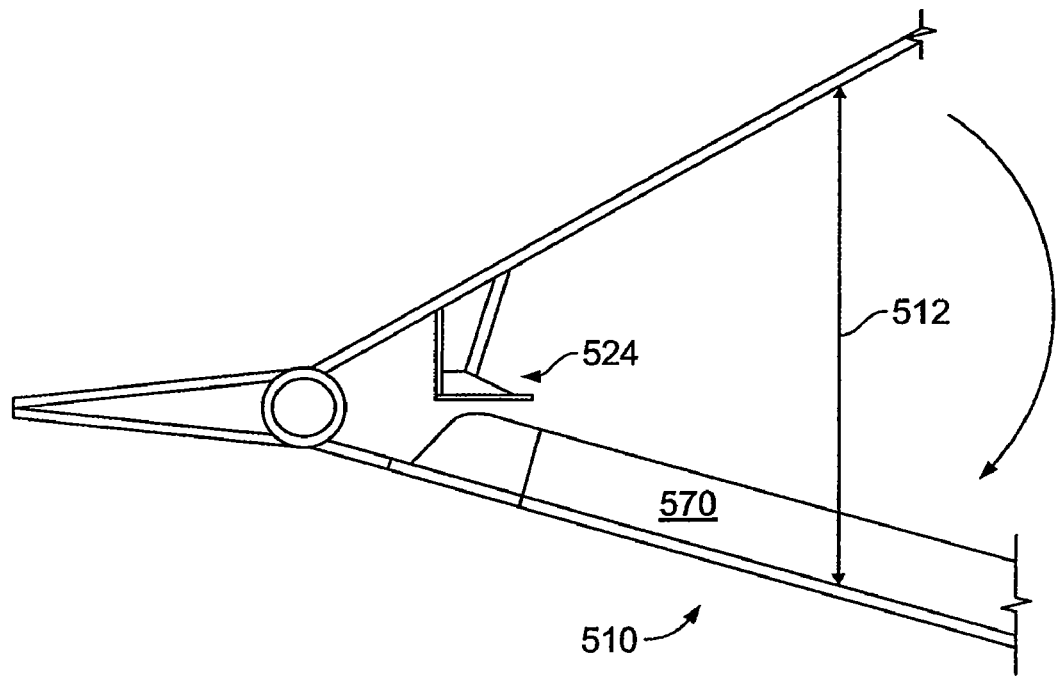
FIG. 11 is a side view of a sixth embodiment of the present invention in the first, unopened position.
Figure 12:
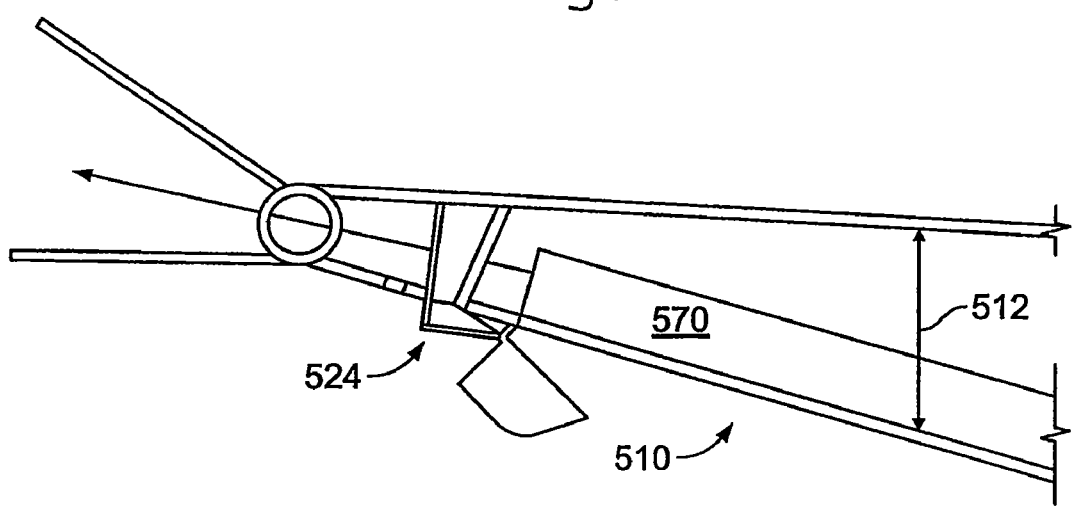
FIG. 12 is a side view of the sixth embodiment as seen in FIG. 11, in the second, opened position.

FIGS. 11 through 17 depict embodiments of the present invention employing differing embodiments of an opening apparatus similar to the opening apparatuses described above. FIGS. 11 and 12 depict opening apparatus 524, which engages and cracks a seal formed on cartridge 570 when handle apparatus 512 is moved from the first handle position, depicted in FIG. 11, to the second handle position, depicted in FIG. 12.

Figure 13:
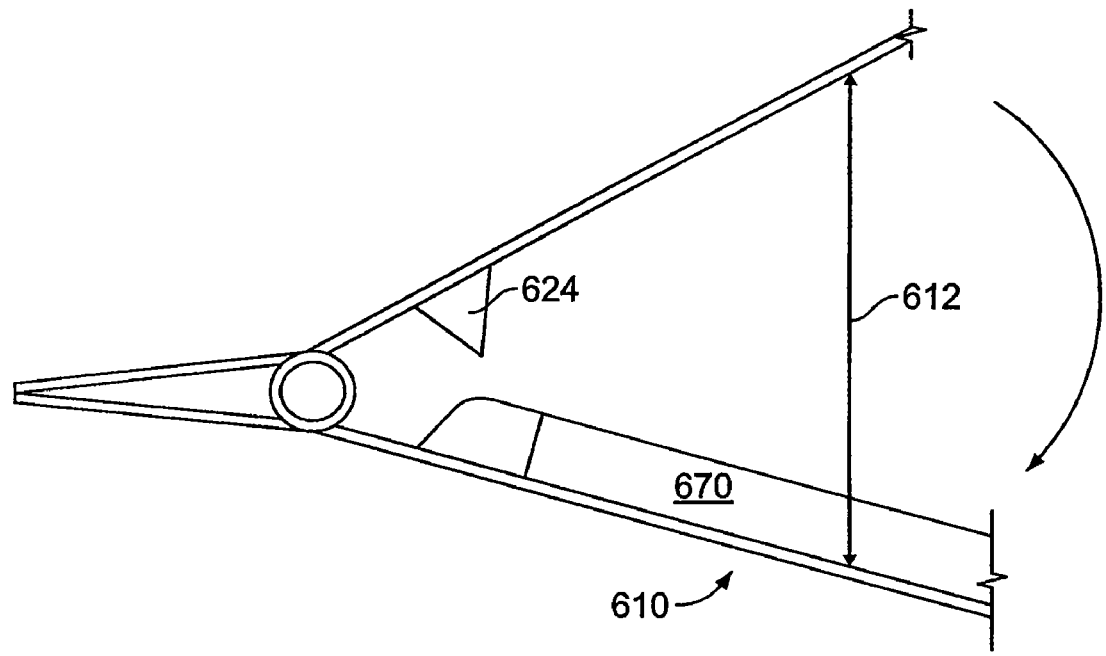
FIG. 13 is a side view of a seventh embodiment of the present invention in the first, unopened position.
Figure 14:
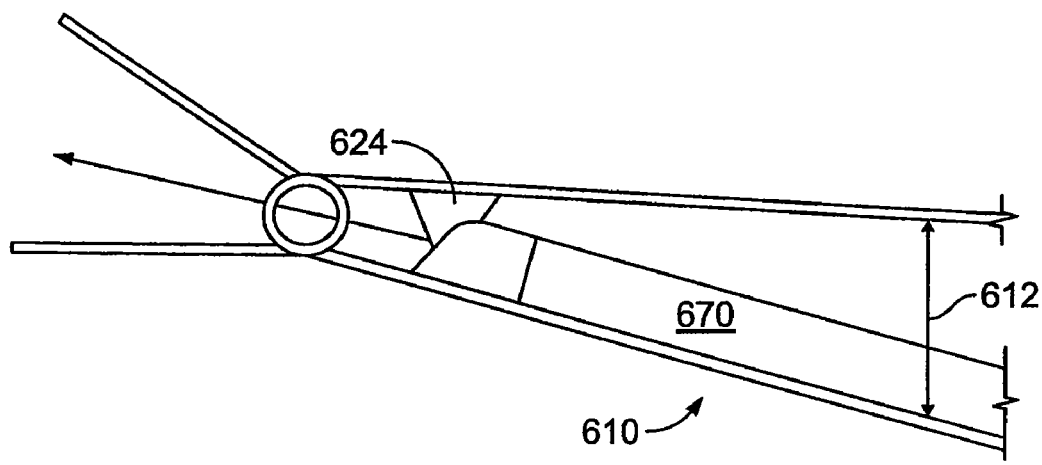
FIG. 14 is a side view of the seventh embodiment of FIG. 13, in the second, opened position.

FIGS. 13 and 14 depict applicator 610, which comprises opening apparatus 624. As seen, opening apparatus 624 engages and pierces medicament cartridge 670 when handle apparatus 612 is moved from the first handle position, depicted in FIG. 13, to the second handle position, depicted in FIG. 14.

Figure 15:
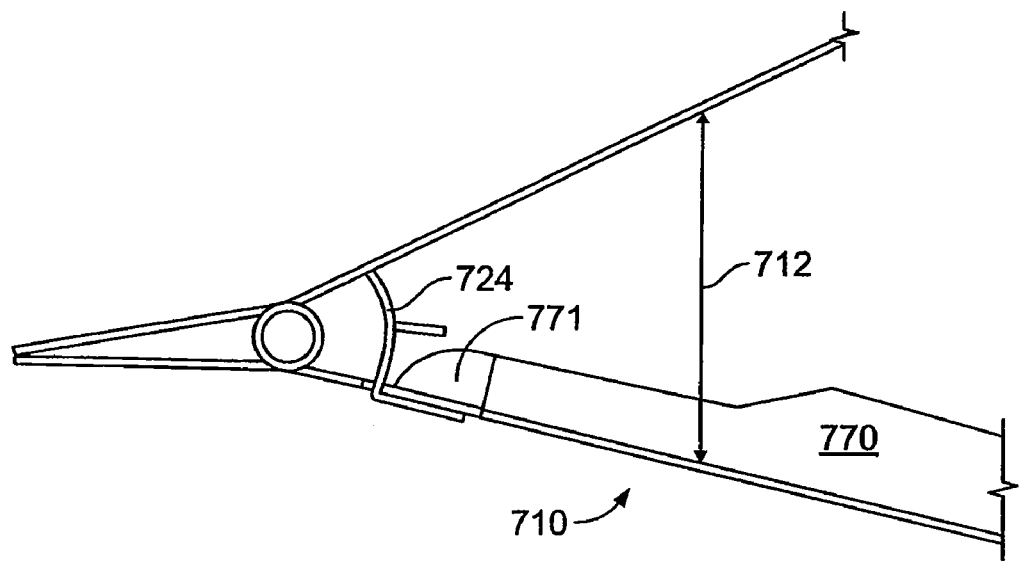
FIG. 15 is a side view of an eighth embodiment of the present invention in the first, unopened position.
Figure 16:
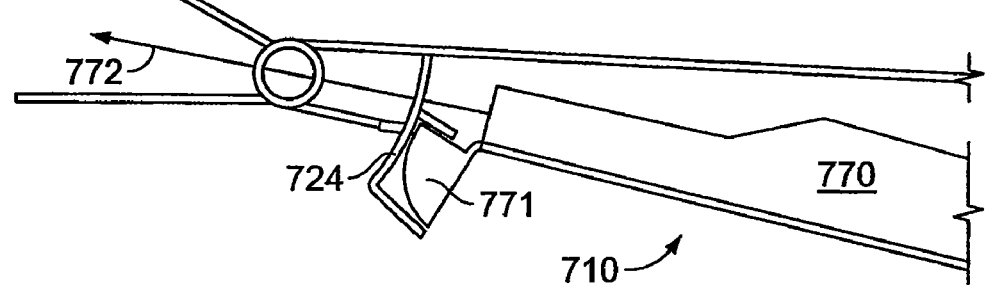
FIG. 16 is a side view of the eighth embodiment as seen in FIG. 15, in the second, opened position.
Figure 17:
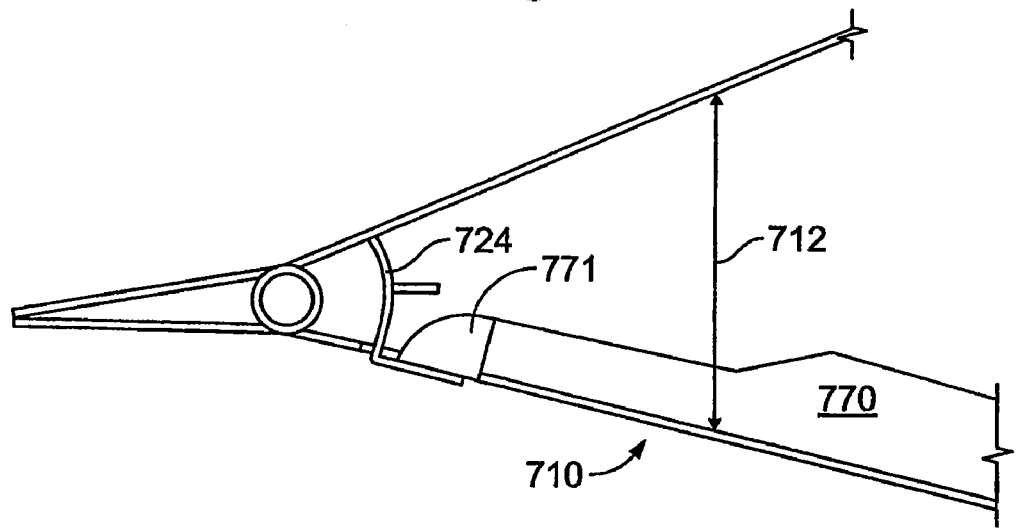
FIG. 17 is a side view of the eighth embodiment as seen in FIG. 15, returned to the first, unopened position.

FIGS. 15 through 17 depict applicator 710, and the progression of opening apparatus 724 in use. As seen, FIG. 15 depicts handle apparatus 712 in the first handle position. When handle apparatus 712 is moved to the second handle position, depicted in FIG. 16, opening apparatus 724 engages tip 771 of cartridge 770, thus opening cartridge 770. This allows medicament (not shown) to flow from cartridge 770 along line 772 to the intended target, such as the skin of an animal, or other substrate. When handle apparatus 712 is returned to the first handle position, as depicted in FIG. 17, opening apparatus 724 again engages tip 771, moving it to the position depicted in FIG. 17, thus closing cartridge 770, preventing medicament from flowing from cartridge 770.

It will be appreciated by those in the art that any of the opening apparatuses depicted in FIGS. 11 through 17 may be used with any applicator embodiment disclosed herein, except for the embodiment disclosed in FIGS. 21 and 22. It will likewise be appreciated by those in the art that any compressing apparatus disclosed in any of FIGS. 1 through 20 may be used with any embodiment of an applicator disclosed herein, except for the embodiment disclosed in FIGS. 21 and 22.

FIG. 18 depicts a ninth embodiment of the present invention. As seen, the ninth embodiment has several features in common with the previous embodiments. For example, applicator 1010 comprises handle apparatus 1012, which comprises first handle member 1013 and second handle member 1014, compressing apparatus 1026, retainer 1022, and opening apparatus 1024, which cracks medicament cartridge 1070, as described above. As seen, retainer 1022 is slightly raised such that medicament cartridge 1070 is not directly engaged to handle member 1014. In this manner, tip 1071 of medicament cartridge 1070, when closed as in Fig. Y, is centered between handle members 1013 and 1014. Handle apparatus 1012 is movable between a first handle position, depicted in FIG. 18, and a second handle position, depicted in FIG. 19.

The embodiment depicted in FIG. 19 comprises a hinge member 1040. However, unlike the previous embodiments, hinge member 1040 comprises two hinges, 1041 and 1042. In this manner, medicament cartridge 1070 may extend through hinge member 1040.

Figure 20:
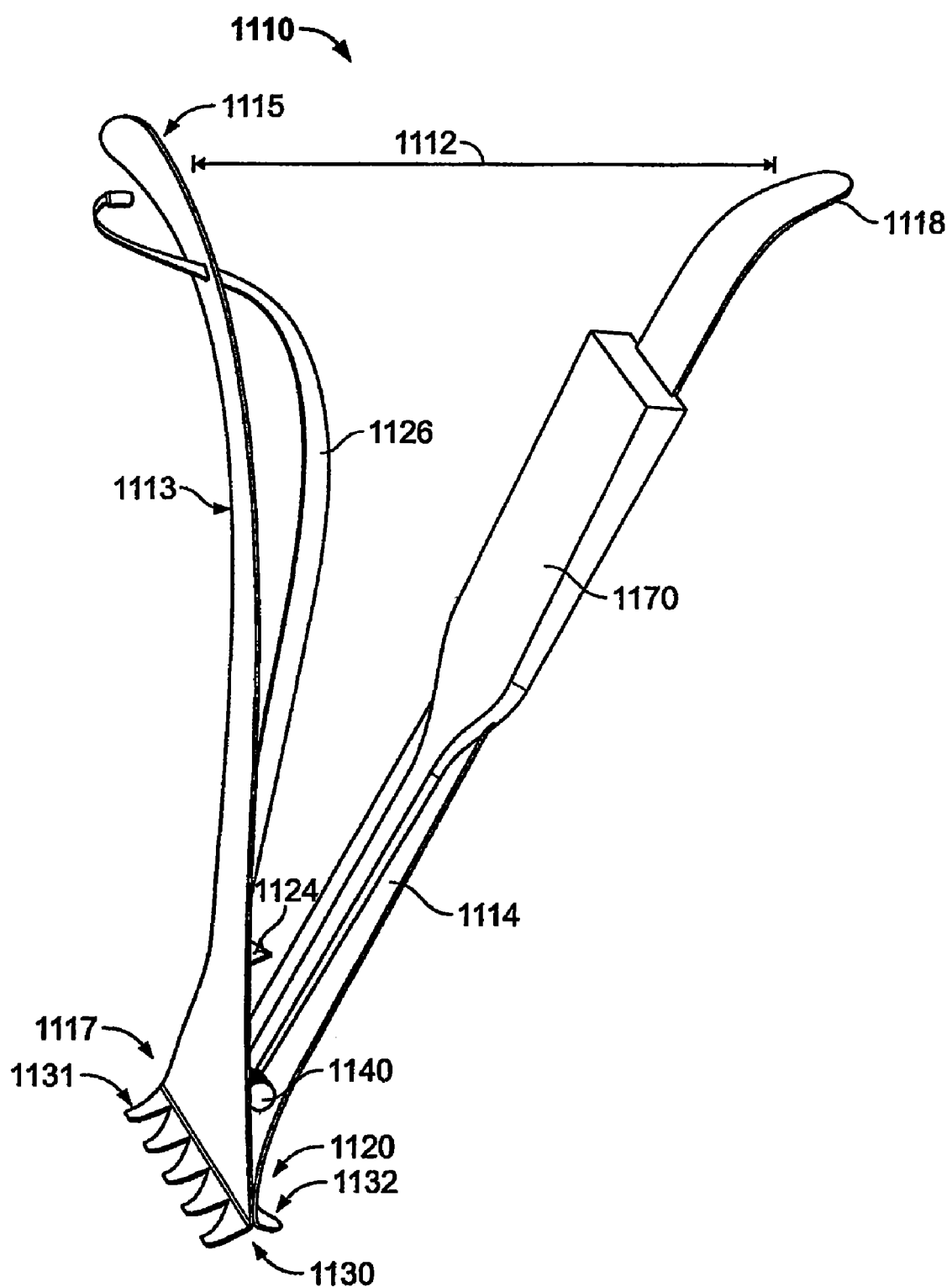
FIG. 20 is a perspective view of a tenth embodiment of the present invention.

FIG. 20 depicts a tenth embodiment of the present invention, which is similar to the embodiments of FIGS. 1 and 2. As seen in FIG. 20, in applicator 1110, cartridge 1170 is integrally formed with second handle member 1114. It will be appreciated by those in the art that, like the embodiment depicted in FIG. 20, the present invention contemplates that in any of the embodiments depicted herein, the medicament cartridge may be removably secured to the applicator, or the medicament cartridge may be integrally formed from/with the applicator.

FIGS. 21 and 22 depict an eleventh embodiment of the present invention. As seen, applicator 910 comprises nearly the same elements as the above-described embodiments. By way of example, applicator 910 comprises handle apparatus 912, which comprises a first handle member 913 and a second handle member 914. Handle apparatus 912 is movable between a first handle position, depicted in FIG. 21, and a second handle position, as described more fully below.

As seen, applicator 910 further comprises separating apparatus 930. In the depicted embodiment, separating apparatus 930 comprises first hair comb 931, and second hair comb 932. In applicator 910, each hair comb 931 and 932 is a rotating brush. Additionally, each rotating brush 931 and 932 can rotate between a first brush position, depicted in FIG. 21, and a second brush position. As described more fully below, and as will be apparent to those in the art, rotating brush 931 rotates in the opposite direction from rotating brush 931. Moreover, the first and second brush positions correspond to first and second handle member positions.

As seen, each hair brush 931 and 932 is engaged to second handle member 914 by way of a pair of struts 946 and a pair of struts 947, respectively. As seen, a first strut of struts 946 engages the front side of brush 931, as shown in FIG. 21. Likewise, the second strut of struts 946 engages the rear side of brush 931, the side opposite that shown in FIG. 21. Struts 947 engage brush 932 in a similar manner. In this manner, movement of second handle member 914 with respect to first handle member 913 causes rotation of each hair brush 931 and 932 as described more fully below.

Applicator 910, like the previously described embodiments, can be used with a medicament cartridge, such as cartridge 970. In order to better facilitate the use of such a cartridge, applicator 910 further comprises retainer 922 and compressing apparatus 926. Retainer 22 is formed on frame 927 of applicator 910. As seen, medicament cartridge 970 is placed in, and secured by, retainer 922.

As stated above, applicator 910 further comprises compressing apparatus 926. Compressing apparatus 926 comprises first compressor 936, which is formed on first hair brush 931, and second compressor 937, which is formed on second hair brush 932. In the embodiment depicted in FIGS. 21 and 22, each compressor 936 and 937 rotates with each respective hair brush 931 and 932. In this manner, as separating apparatus 930 moves from the first brush position to the second brush position, compressors 936 and 937 engage medicament cartridge 970.

In use, applicator 910 works in a similar fashion to the applicators described above. The user places medicament cartridge 970 in retainer 922. The user next places both brushes 931 and 932 of separating apparatus 930 on, for example, an animal. The user then compresses handle members 913 and 914, moving them from the first handle position, depicted in FIG. 21, to the second handle position. The movement of second handle member 914 causes hair brushes 931 and 932 to rotate, parting any hair engaged to the hair brushes and exposing the skin (or other substrate) underneath. In the depicted embodiment, movement of second handle member 914 up causes hair brush 931 to rotate clockwise and brush 932 to move counter-clockwise, as depicted in FIG. 21. Moving handle members 913 and 914 to the second handle position also causes compressing apparatus 926 to engage medicament cartridge 970, compressing cartridge 970 and expelling any medicament from cartridge 970.

While specific configurations of the invention have been described in detail, it will be appreciated by those skilled in the art that various modifications and alternatives to those details could be developed in light of the overall teachings of this disclosure. The particular arrangements disclosed herein are meant to be illustrative only and not limited as to the scope of the invention which is to be given the full breadth of the appended claims and any equivalents thereof.

What is claimed is:

1. A medicament applicator for use with a medicament cartridge, the applicator comprising:
    a handle apparatus, comprising a first handle member and a second handle member, wherein the first handle member and the second handle member are movable with respect to one another between a first handle position and a second handle position;
    a separating apparatus attached to and driven by the handle apparatus, the separating apparatus comprising a first separating member and a second separating member and movable between a first separating position, which corresponds to the first handle position, and a second separating position, which corresponds to the second handle position, wherein the first separating member has a first separating end distally positioned from the first handle member, and the second separating member has a second separating end distally positioned from the second handle member, and wherein the first and second separating ends are in proximity to one another without crossing each other when the first and second handle members are in the first handle position;
    a compressing apparatus attached to the applicator, wherein the compressing apparatus compresses the medicament cartridge expelling the medicament from the medicament cartridge when the first and second handle members move from the first position toward the second position; and,
    an opening apparatus formed on the first handle member, wherein the opening apparatus opens the medicament cartridge when the first and second handle members move from the first handle position toward the second handle position;
    wherein the opening apparatus opens the medicament cartridge by piercing the cartridge.

2. The medicament applicator as set forth in claim 1, wherein the opening apparatus opens the medicament cartridge by cracking a seal formed on the cartridge.

3. The medicament applicator as set forth in claim 1, wherein the opening apparatus closes the medicament cartridge when the first and second handle members are moved from the second position to the first position.

4. The medicament applicator as set forth in claim 1, wherein the first and second separating members comprise a first and second hair comb at the first and second separating ends, respectively, and wherein the first hair comb is integrally formed from the first handle member, and the second hair comb is integrally formed from the second handle member.

5. The medicament applicator as set forth in claim 4, wherein the first handle member is hingedly engaged to the second handle member.

6. The medicament applicator as set forth in claim 5, further comprising at least one biasing spring engaged to the first and the second handle member, wherein the at least one biasing spring biases the first and the second handle member to the first handle position.

7. The medicament applicator as set forth in claim 1, wherein the compressing apparatus is attached to the first handle member and comprises a tensioned lever.

8. The medicament applicator as set forth in claim 1, wherein the medicament cartridge is removably secured to the applicator.

9. The medicament applicator as set forth in claim 8, further comprising a retainer formed on the second handle member, wherein the medicament cartridge is secured within the retainer.

10. The medicament applicator as set forth in claim 1, wherein the separating apparatus comprises a first rotating brush and a second rotating brush, wherein movement of the first and second handle members from the first position to the second position causes the first rotating brush to rotate in a first direction and causes the second rotating brush to rotate in a second direction, opposite the first direction.

11. The medicament applicator as set forth in claim 10, wherein the compressing apparatus comprises a first compressing member engaged to the first rotating brush, and a second compressing member engaged to the second rotating brush.

12. The medicament applicator as set forth in claim 10, wherein the medicament cartridge is removably secured to the applicator.

13. The medicament applicator as set forth in claim 1, wherein the compressing apparatus compresses the medicament cartridge by contact therewith expelling the medicament from the medicament cartridge when the first and second handle members move from the first position toward the second position.

14. The medicament applicator as set forth in claim 1, wherein the first and second separating ends begin in a position in proximity to one another which corresponds to the first handle position and spread significantly apart to a position which corresponds to the second handle position.

15. A medicament applicator for use with a medicament cartridge, the applicator comprising:
    a handle apparatus, comprising a first handle member and a second handle member, wherein the first handle member and the second handle member are movable with respect to one another between a first handle position and a second handle position;
    a separating apparatus attached to and driven by the handle apparatus, the separating apparatus comprising a first separating member and a second separating member and movable between a first separating position, which corresponds to the first handle position, and a second separating position, which corresponds to the second handle position, wherein the first separating member has a first separating end distally positioned from the first handle member, and the second separating member has a second separating end distally positioned from the second handle member, and wherein the first and second separating ends are in proximity to one another without crossing each other when the first and second handle members are in the first handle position;

a compressing apparatus attached to the applicator, wherein the compressing apparatus compresses the medicament cartridge expelling the medicament from the medicament cartridge when the first and second handle members move from the first position toward the second position;

an opening apparatus formed on the first handle member, wherein the opening apparatus opens the medicament cartridge when the first and second handle members move from the first handle position toward the second handle position; and wherein the opening apparatus opens the medicament cartridge by cracking a seal formed on the cartridge.

16. A medicament applicator for use with a medicament cartridge, the applicator comprising:

a handle apparatus, comprising a first handle member and a second handle member, wherein the first handle member and the second handle member are movable with respect to one another between a first handle position and a second handle position;

a separating apparatus attached to and driven by the handle apparatus, the separating apparatus comprising a first separating member and a second separating member and movable between a first separating position, which corresponds to the first handle position, and a second separating position, which corresponds to the second handle position, wherein the first separating member has a first separating end distally positioned from the first handle member, and the second separating member has a second separating end distally positioned from the second handle member, and wherein the first and second separating ends are in proximity to one another without crossing each other when the first and second handle members are in the first handle position;

a compressing apparatus attached to the applicator, wherein the compressing apparatus compresses the medicament cartridge expelling the medicament from the medicament cartridge when the first and second handle members move from the first position toward the second position;

an opening apparatus formed on the first handle member, wherein the opening apparatus opens the medicament cartridge when the first and second handle members move from the first handle position toward the second handle position; and wherein the opening apparatus closes the medicament cartridge when the first and second handle members are moved from the second position to the first position.

* * * * *